United States Patent [19]
Wiederin

[11] Patent Number: 5,212,365
[45] Date of Patent: May 18, 1993

[54] DIRECT INJECTION MICRO NEBULIZER SYSTEM AND METHOD OF USE

[75] Inventor: Daniel R. Wiederin, Omaha, Nebr.

[73] Assignee: Cetac Technologies, Inc., Omaha, Nebr.

[21] Appl. No.: 813,766

[22] Filed: Dec. 27, 1991

[51] Int. Cl.[5] .............................................. B23K 9/00
[52] U.S. Cl. ....................... 219/121.520; 219/121.480; 219/121.590; 315/111.51
[58] Field of Search ....................... 219/121.59, 121.51, 219/121.52, 121.48; 315/111.51, 111.21; 356/316; 239/338, 341–343, 432

[56] References Cited

U.S. PATENT DOCUMENTS

| | | |
|---|---|---|
| 4,084,934 | 4/1978 | Kumazawa. |
| 4,177,945 | 12/1979 | Schwartz et al. |
| 4,206,160 | 6/1980 | Suddenderf et al. |
| 4,251,033 | 2/1981 | Rich et al. |
| 4,551,609 | 11/1985 | Falk. |
| 4,575,609 | 3/1986 | Fassel et al. |
| 4,739,147 | 4/1988 | Meyer et al. |
| 4,746,067 | 5/1988 | Svoboda. |
| 4,833,294 | 5/1989 | Montaser et al. ............... 315/111.51 |
| 4,926,021 | 5/1990 | Strevsard et al. ............... 315/111.51 |
| 4,990,740 | 2/1991 | Meyer. |
| 5,083,004 | 1/1992 | Wells et al. ..................... 219/121.52 |

OTHER PUBLICATIONS

K. E. Lawrence et al., Anal. Chem., 56, p. 289, 1984.
K. E. LaFreniere et al., Spectrochim. Acta., 40B, p. 1495, 1985.
K. E. LaFreniere et al., Anal. Chem., 59, p. 879, 1987.
D. R. Wiederin et al., Anal. Chem., 63, p. 219, 1991.
D. R. Wiederin et al., Anal. Chem., 63, p. 1627, 1991.
D. R. Wiederin et al., R. S. Houk, Appl. Spectrosc., 45, p. 1408, 1991.
Winkler et al., Anal. Chem., 60, p. 489, 1988.

*Primary Examiner*—Mark H. Paschall
*Attorney, Agent, or Firm*—James D. Welch

[57] ABSTRACT

A direct injection micro nebulizer system for use in nebulizing sample solutions in close proximity to sample analysis systems, is disclosed. The present invention offers design features and utility not available in previously known micro nebulizer systems. The present invention, preferably, provides single piece unibody construction of the primary body element, and construction of all element thereof from nonmetallic, hydrofloric acid resistant materials. The present invention allows easy cleaning and adjustment of element relationships which are necessary to proper operation of direct injection micro nebulizer systems. Use of separate or integrated protective sleeving on otherwise crushable sample solution delivery tubing is also disclosed. Use of the direct injection micro nebulizer with standard and specially designed inductively coupled plasma torches, as well as other sample analysis systems is disclosed.

27 Claims, 2 Drawing Sheets

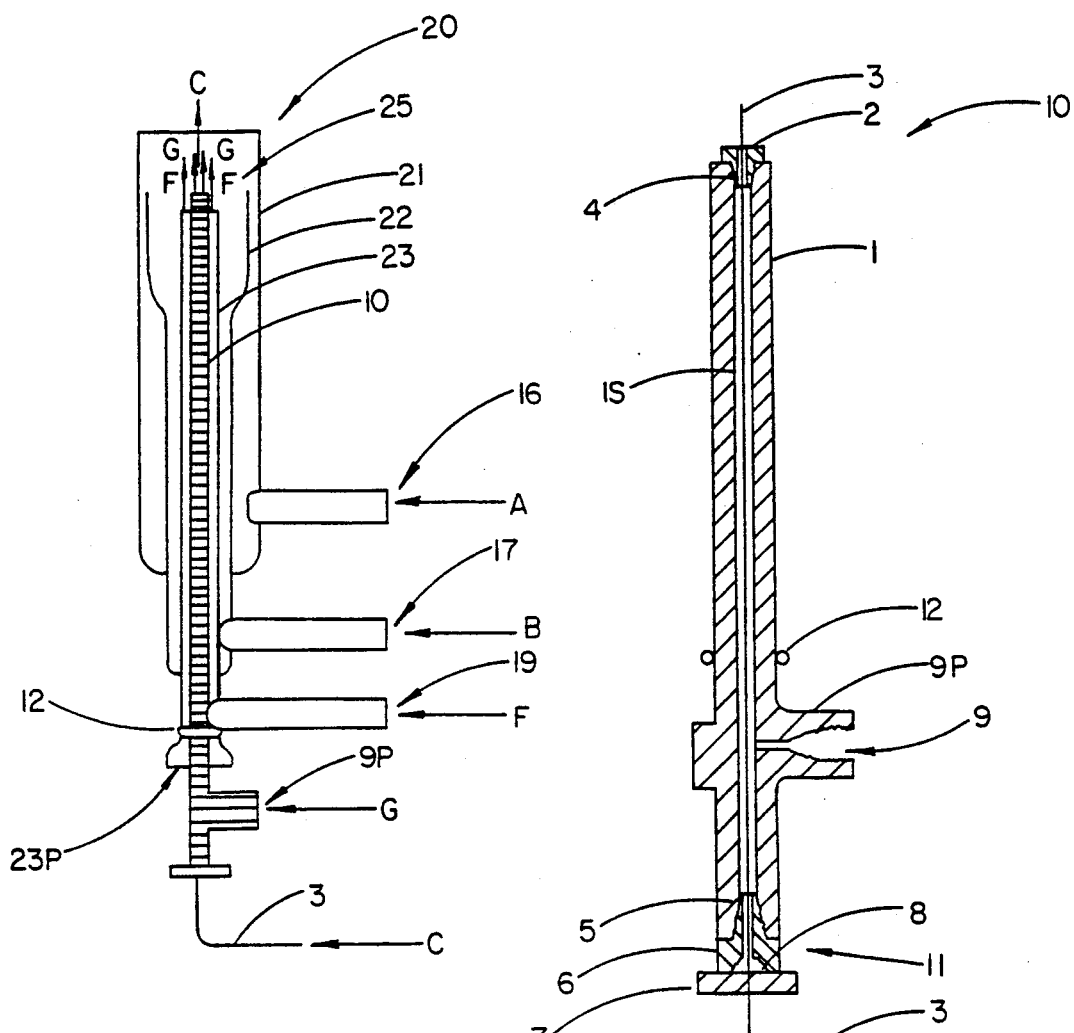
FIG 2
FIG 1a
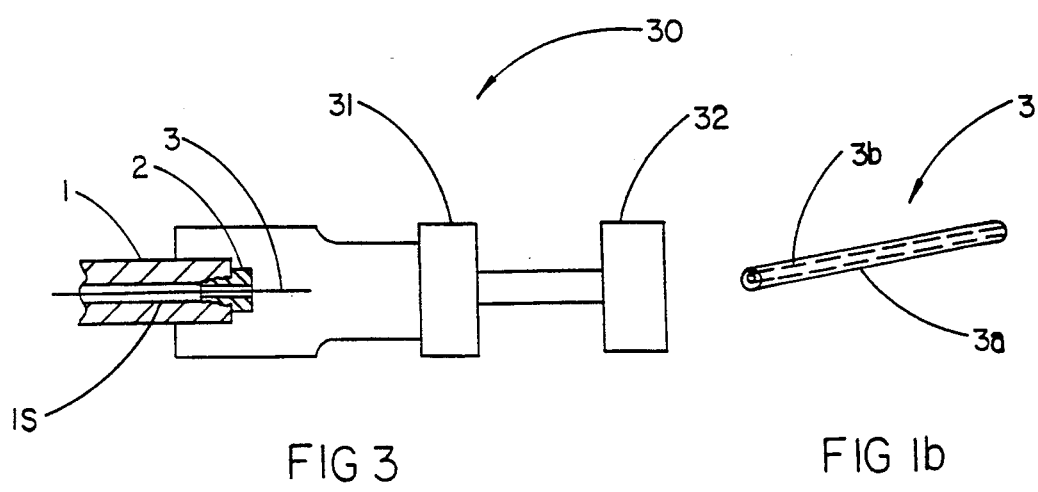
FIG 3
FIG 1b

DIRECT INJECTION MICRO NEBULIZER SYSTEM AND METHOD OF USE

TECHNICAL FIELD

The present invention relates to systems and methods for use in analysis of samples, and more particularly to a small internal volume, easy to use total consumption micro nebulizer system which directly nebulizes and injects sample solutions into closely situated sample analysis systems.

BACKGROUND

The use of sample solution nebulizer systems to introduce liquid samples into sample analysis systems is well known. Sample solution nebulization is typically accomplished by known mechanical, pneumatic or ultrasonic means for instance, and sample analysis systems which can be used include Inductively Coupled Plasma (ICP), other plasma based systems, and mass spectrometers.

Typically, sample solution nebulization is carried out in an aerosol chamber at a location remote from a sample analysis system, and nebulized sample droplets must be transported to the location of the sample analysis system by way of a connection means. A common problem which occures during use is that nebulized sample is lost by adherence to the internal walls of the aerosol chamber and connection means between the output of the sample nebulizer system and the input to the sample analysis system. Additionally, the aerosol chamber and connecting means volume must be filled with nebulized sample to cause nebulized sample to eject from said connection means into the remotely located sample analysis system. A relatively larger amount of nebulized sample must then be prepared than would be the case if the sample nebulizer system had no aerosol chamber and was situated in closer proximity to the sample analysis system. System sensitivity is, as a result, adversely affected and tedious, time consuming, system flushing procedures are often required to prevent sample carry-over from one analysis procedure from contaminating subsequent analysis procedure results. It would then, be very beneficial if a sample nebulizer system which did not require an aerosol chamber and which could be positioned closely adjacent to sample analysis systems were available.

In view of the identified problems, Fassel et al., designed a "micro nebulizer" system and obtained a Patent thereon in 1986, said Patent being U.S. Pat. No. 4,575,609. The Fassel et al. teachings are that the micro nebulizer should be inserted directly into a standard torch of the type used in Inductively Coupled Plasma sample analysis, in which standard torch, during use, a plasma is formed. The micro nebulizer is designed to perform sample solution nebulization directly. That is, the aerosol chamber and connection means internal volume between the sample nebulizer system and a remotely located sample analysis system is eliminated.

The Fassel et al. invention assumes the presence of a first tube, which first tube is essentially the sample injector tube of a standard torch. Briefly, to aid with understanding, a standard torch is comprised of a series of elongated concentric tubes, which concentric tubes are typically, but not necessarily, made of quartz. The centermost tube is typically termed the sample injector tube. It is typically circumscribed by an intermediate tube, which intermediate tube is typically circumscribed by an outer tube. One can visualize the torch system in side elevation, from a position perpendicularly removed therefrom, with the longitudinal dimensions of the various elongated tubes projecting vertically upward from an underlying horizontal surface. Sample particles from a typical sample nebulizing system are typically injected vertically into the sample injector tube of the standard torch from a sample access port at the vertically lower aspect thereof, and caused to flow through said sample injector tube to the upper aspect thereof under the influence of a pressure gradient, whereat they are ejected into the space above said upper aspect of the sample injector tube, which space is typically within the volume circummscribed by the outer tube of the standard torch system, in which space a plasma is typically created. As well, typically tangentially injected gas flows are typically entered into the annular spaces between the outer surface of the sample injector tube and the inner surface of the intermediate tube, and between the outer surface of the intermediate tube and the inner surface of the outer tube. (Note, tangential is to be understood to mean that a gas flow follows a spiral-like upward locus path from its point of entry to the standard torch). The typically tangential gas flows are entered by way of intermediate and outer ports also present in the torch. Said typically tangentially injected gas flows serve to shield the various tubes which they contact from the intense temperatures and heat formed by creation of a plasma in the upper aspects of the torch, and to some extent aid sample flow into the plasma associated area.

The Fassel et al. invention teaches that rather than enter a previously, distally, nebulized sample to the sample access port of a standard torch, a micro nebulizer should be entered into the sample injector port and positioned so that the upper aspect thereof is at an essentially equal vertical level with the upper aspect of the sample injector tube of the standard torch, into which the micro nebulizer is inserted. Sample solution is then entered into the micro nebulizer via a sample delivery inner tube, directly, without any prior sample nebulization being performed thereon. The Fassel et al. micro nebulizer is designed to cause sample solution entered thereto, to eject from the upper aspect of the micro nebulizer and, be nebulized thereat. The upper aspect of the sample delivery inner tube thereof, is positioned at essentially the same vertical level as the upper aspect of the sample injector tube of the standard torch, hence, is located very near the position at which a plasma can be created for use in analysis of the ejected nebulized sample. It will be appreciated that the only nebulizer internal volume which exists is that within the micro nebulizer and the associated connection means thereto from the source of sample solution. Said internal volume is typically on the order of five (5) microliters and is orders of magnitude smaller than the internal volume associated with the sample injector tube of a standard torch and the connecting means thereto from a remotely located conventional sample solution nebulizer system.

To better understand the Fassel et al. micro nebulizer it is necessary to better describe the system thereof. Basically, the Fassel et al. micro nebulizer is comprised of an inner tube and an outer tube, which inner tube is concentrically circumscribed by said outer tube. The two concentric tubes are oriented vertically and placed into the first tube, which first tube can be thought of as the sample injector tube of a standard torch as described above. A sample solution of can be entered into the micro nebulizer at the lower aspect of the inner tube thereof and caused, under the influence of a pressure gradient, (typically 100 to 1000 psi), to flow vertically upward and eject from the upper aspect of the inner tube of the micro nebulizer. Sample solution velocities on the order of one-hundred (100) meters-per-second are common. In addition, a gas flow can be entered into the annular space between the outer surface of the inner tube and the inner surface of the outer tube of the micro nebulizer, which gas flow interacts with the sample solution flow at the point of its ejection from the inner tube of the micro nebulizer, thereby causing said sample solution to be nebulized by essentially pneumatic means. An additional gas flow can be injected into the annular space which results between the outer surface of the outer tube of the micro nebulizer and the inner surface of the sample injector tube of the standard torch into which the Fassel et al. micro nebulizer is inserted. Said gas flow can also aid with the sample solution nebulization effect. The nebulized sample solution then immediately injects into the space in the standard torch in which a plasma can be created. The disclosure of the Fassel et al. Patent teaches that a support tube should be epoxied to the outer surface of the outer tube of the micro nebulizer, along some portion thereof which is inside the first tube, (ie. sample injector tube of the standard torch), during use, apparently to protect the outer and inner tubes thereof against being crushed when inserted into the sample injector tube of the standard torch, and to aid with a firm fit within the sample injector tube of the standard torch into which the micro nebulizer is inserted. The Fassel et al. disclosure teachings also indicate that the outer and inner tubes of the micro nebulizer should be attached to the standard torch by way of a fixed fitting, and that the upper aspect of the inner tube of the micro nebulizer should be positioned vertically at a level below the upper aspect of the sample injector tube of the standard torch. The drawings of Fassel et al. show that the upper aspect of said inner tube of the micro nebulizer is also placed vertically below the upper aspect of the outer tube of the micro nebulizer and that said outer tube of the micro nebulizer and the sample injector tube of the standard torch are tapered inwardly at their upper aspects. In use, it has been found, that the Fassel et al. system as described above, particularly when used with high solids content sample solutions, becomes clogged at the upper aspect thereof. This results in the necessity that the micro nebulizer be cleaned often, which cleaning is difficult to perform and often leads to breakage of the micro nebulizer. It has also been discovered that the upper aspect of the inner tube of the Fassel et al. system is difficult to position inside the outer tube of the Fassel et al. system, and that the Fassel et al. system tends dislodge from the point at which it is secured inside the standard torch sample injector tube at the lower aspect of said sample injector tube, when relatively high pressure gas flow is entered into the annular space between the outer surface of the outer tube of the micro nebulizer and the inner surface of the sample injector tube of the standard torch. It is emphasised that the securing of the micro nebulizer to the inside of the sample injector tube of the standard torch is by way of a fitting, through which fitting is run the outer and inner tubes of the micro nebulizer.

In view of the above, users of the Fassel et al. system have found that great utility would result from modifying the Fassel et al. system to provide means which allow a user thereof to:

1. easily access the inner portion of the upper aspect of the micro nebulizer; and 2. easily insert the inner tube of the micro nebulizer and adjust the vertical location of the upper aspect thereof independent from any interaction with the outer tube thereof.

Other improvements in the Fassel et al. system would result from use of a protective sleeve around at least a portion of the extent of the inner tube thereof, use of hydrofloric acid resistant nonmetalic materials in the construction thereof, and use of a unibody design for the basic portion of the micro nebulizer, which unibody design allows for connections at the lower, middle and upper vertical aspects thereof. The connection at the upper aspect thereof being to allow easy access and cleaning of accumulated sample solids, the connection at the lower aspect thereof being to allow inner tube upper aspect vertical level positioning, and the connection at the middle thereof being to allow attachment to a source of gas to cause a flow thereof into the annular space between the outer surface of the inner tube of the micronebulizer and the inner surface of outer tube thereof, which outer tube thereof would be formed by the unibody design of the micro nebulizer. The use of only nonmetalic materials is proposed to prevent untoward interaction with plasma energy which is common when metals are present near a plasma, and the use of hydrofloric resistant materials, (eg. polyimides), is proposed to allow use of hydrofloric acid as a sample solvent.

Another very recent Patent, U.S. Pat. No. 4,990,740 to Meyer, recognizes the benefits and problems associated with the Fassel et al. micronebulizer, and teaches an Intraspray ICP Torch which serves to overcome some of said problems. The Meyer invention, in essence, provides a low operational pressure equivalent to a micronebulizer system at the lower aspect thereof, and also provides a series of impactors thereabove in a torch system portion of the invention. The Meyer invention provides greater stability in both construction and in nebulized sample solution flow to an ICP. Said impactors serve to deflect large diameter droplets (eg. over approximately fifteen (15) microns in diameter), and prevent their ejection from the upper aspect of the invention, and in addition to buffer the ejected flow of nebulized sample solution.

In view of the benefits provided by the Fassel et al. micro nebulizer, and in view of the difficulties associated with use thereof, which difficulties have received recognition form users thereof, there is thus demonstrated a need for an improved direct injection micro nebulizer.

DISCLOSURE OF THE INVENTION

The objectives identified in the Background Section of this Disclosure are achieved by the present invention.

The present invention is a total consumption Direct Injection Micro Nebulizer System which can be inserted into the space within a sample injector tube of a standard torch, as described with respect to the Fassel et al. invention in the Background Section of this Disclosure, or into specially designed torches which, for instance, have no sample injector tube present. The present invention also accepts a sample solution which has not been subject to prior nebulization and typically injects it into a closely situated plasma in a sample analysis system, performing required sample solution nebulization directly, again much as taught in the Fassel et al. Patent. The present invention, however, provides utility not taught in Fassel et al. and can be used with sample analysis systems other than those utilizing torches and plasmas as it does not require the presence of an ICP torch sample injector tube as part of its construction.

The present invention is, in its preferred embodiment, comprised of a system of a primary body element, a top element, a double nut element system, or functionally equivalent sample delivery tube system adjustment means, and a sample delivery tube which is typically encompassed within a separate or integral protective sleeve over at least a portion of its length, to form the sample delivery tube system.

The primary body element of the present invention is preferably, but not necessarily, of unibody construction and is generally elongated in shape with a distinct longitudinal dimension, and with a centrally located hole extending longitudinally therethrough. At the upper aspect of the primary body element, as it is viewed in side elevation from a position perpendicularly removed therefrom, with the longitudinal dimension thereof projecting vertically upward, perpendicular to an underlying horizontal surface, is located a first connection means, which first connection means typically comprise female screws threads. A top element, which has a centrally located longitudinally oriented hole therethrough and which has connection means oriented parallel to the locus of said hole, which connection means are complimentary to said first connection means at the upper aspect of the primary body element, is also typically present and removably attached to the primary body element by way of said connection means. The top element can be of an elongated design which provides means for positioning the upper aspect of the top element near a plasma in an inductively coupled plasma torch, while maintaining the attached primary body element of the direct injection nebulizer system at some distance therefrom. At the lower aspect of the primary body element there is present a second connection means, again comprising, typically, female screw threads. A double nut element system, or functionally equivalent sample delivery tube system adjustment means, which has a centrally located longitudinally oriented hole therethrough and which has connection means thereon, which connection means are complimentary to the second connection means at the lower aspect of the primary body element, is also present and removably attached to the primary body element by way of said second connection means. In one embodiment of the present invention a chromatography column can be attached to the sample provision tube system at the lower aspect of the sample delivery tube system adjustment means to allow temporal preseparation of sample components in a multi-analyte component sample solution prior to entry thereof into the direct injection nebulizer system. (Note, a chromatography column causes various analyte components in a sample solution to move therethrough, as the containing sample solution is passed therethrough, at varying rates based upon, for instance, varying affinities for the various components by the materials present in the chromatography column.) Also present on said primary body element is a third connection means which provides access to the centrally located longitudinally oriented hole which projects through the primary body element.

The sample delivery tube of the present invention is typically, over at least the portion of its length extending from the lower aspect of the sample delivery tube system adjustment means, encompassed within a separate or integral protective sleeve, and the combination sample delivery tube and protective sleeve, forming a sample deliver tube system, is threaded into the centrally located longitudinally oriented hole through the double nut element system, or functionally equivalent sample delivery tube system adjustment means. The sample delivery tube per se, (ie. the sample delivery tube system without the protective sleeve), is then, typically, threaded through the centrally located longitudinally oriented hole through the primary body element, then into and out of the centrally located longitudinally oriented hole through the top element, when said top element is present. The top element, when present, is then removably attached to the primary body element by way of the connection means thereon which are complimentary to the first connection means present at the upper aspect of the primary body element. It should be noted that inserting the sample delivery tube into the centrally located longitudinally oriented hole which extends through the top element prior to removably attaching it to the upper aspect of the primary body element facilitates the direct injection nebulizer system construction process. At the lower aspect of the direct injection micro nebulizer system the sample delivery tube system is removably attached to the primary body element, via the upper oriented nut of the double nut element system, or functionally equivalent sample delivery tube system adjustment means, by way of the second connection means present at the lower aspect of the primary body element. The lower nut of the double nut element system firmly grips the sample delivery tube system, and removably attaches to the upper nut of the double nut element, or functionally equivalent sample delivery tube system adjustment means, system by way of connection means thereon. It should be understood that the vertical level of the upper aspect of the sample delivery tube can then be easily adjusted by a user of the present invention by manipulating the upper nut of the double nut element system, or functionally equivalent sample delivery tube system adjustment means, where it removably attaches to second connection means at the lower aspect of the primary body element of the direct injection micro nebulizer system taught herein.

During use with a standard torch and plasma sample analysis system, the present invention, as described above, is inserted into and secured within, the space within the sample injector tube of a standard torch, or within the intermediate tube of a specially designed torch which has no sample injector tube present for instance, such that the upper aspect of the sample delivery tube is positioned just below the position therein at which a plasma can be created for use in the analysis of samples. The vertical level of the upper aspect of the sample delivery tube can be precisely adjusted by manipulation of the double nut element system, or sample delivery tube system adjustment means functional equivalent, as alluded to above. A sample solution is entered into the sample delivery tube, at the end thereof opposed to that present at the upper aspect of the present invention. Said sample solution is forced to move through the sample delivery tube and eject from the upper aspect thereof. In addition, a gas flow is caused to be entered to the third connection means on the primary body element. Said gas flow, under the influence of a pressure gradient, transverses the length of the primary body element in the annular space between the outer surface of the sample delivery tube and the inner surface of the centrally located longitudinally oriented hole through primary body element. At the upper aspect of the primary body element said gas flow is ejected from the upper aspect of the top element when present, from the annular space between the outer surface of the sample delivery tube and the inner surface of the centrally located longitudinally oriented hole through the top element. The ejected sample solution interacts with said ejected gas flow to effectively nebulize the sample solution into sample solution droplets. In addition, an auxiliary sample gas flow can be entered into the annular space between the outer surface of the primary body element of the present invention, and the inner surface of the sample injector tube of the standard torch, if present, by way of an the access port in the standard torch. Said gas flow, again under the influence of a pressure gradient, will eject from the annular space into which it is entered, and interact with the simultaneously ejected sample solution and gas flow described above which is entered to the third connection means of the primary body element. The overall effect being to provide finely nebulized sample solution droplets, and cause same to be vertically swept into the region of the standard, or specially designed, torch in which a plasma can be created. If a specially designed torch which has no sample injector tube present is used, the additional gas flow just described, will of course, not be possible.

The present invention additionally, in the preferred embodiment thereof, is fabricated from hydrofloric acid resistant nonmetallic materials, and the primary body element is firmly but removably secured within the sample injector tube of the standard, or intermediate tube of a specially designed, torch with which it is used, by means of one or more "O" rings which circumscribe the primary body element.

It will be appreciated that the present invention allows a user thereof to easily access the inner space at the upper aspect of the primary body element by removal of the top element. This feature allows easy cleaning of any solid sample build up at said location which might clog the invention. In addition, threading the sample delivery tube into the centrally located longitudinally oriented hole through the top element, when it is present, can be easily performed when the top element is removed from the first connection means at the upper aspect of the primary body element. Also, as alluded to above, the vertical level of the upper aspect of the sample delivery tube can be easily and precisely adjusted by manipulation of the upper nut element of the double nut system, or by manipulation of a functionally equivalent sample delivery tube system adjustment means at its attachment to the second connection means on said primary body element.

Finally, while the use of a standard or specially designed torch, such as typically used in inductively coupled plasma analysis of samples was used as an example in the above, it is to be understood that the present invention could also be inserted into a tube which leads to a mass spectrometer sample analysis system, perhaps by way of a desolvation chamber. In such a system momentum separators, skimmers, roughing pumps and ion focusing lenses etc. might be present. That is to say the present invention can be used with sample analysis systems which require sample nebulization, other than sample analysis systems which utilize standard or specially designed ICP torches and plasmas.

A better understanding of the present invention can be developed by a study of the Detailed Description Section of this Disclosure, with reference to the included drawings.

SUMMARY OF THE INVENTION

The use of sample solution nebulizer systems to prepare samples for analysis is well known. Typically a sample solution is subjected to aerosol chamber contained pneumatic, mechanical or ultrasonic processes, for instance, which cause a sample solution to be nebulized at a location distally situated from a sample analysis system, such as an inductively coupled plasma or mass spectrometry sample analysis system. As a result the nebulized sample must be transported to the sample analysis system through a relatively large internal volume connection means. The aerosol chamber and connection means internal volume is the source of numerous problems. For instance, its presence dictates that a relatively large amount of nebulized sample solution be available to fill same. The sensitivity of the overall sample analysis system is thus reduced. Additionally, said internal volume must often times be flushed out after an analysis procedure to prevent contamination of results obtained in subsequent analysis procedures.

In view of the above identified problems inventors have developed and Patented a Micro Nebulizer for Direct Injection of Samples to a sample analysis system. See U.S. Pat. No. 4,575,609 to Fassel et al. Said Micro Nebulizer is, during use, placed, and performs nebulization, very near associated sample analysis equipment, which in the case of the Fassel et al. invention involves placement in the sample injector tube of an inductively coupled plasma sample analysis system standard torch. The internal volume of the micro nebulizer is, as a result, kept very small, typically on the order of five (5) microliters. The overall effect is that the sensitivity of an overall system using the Fassel et al. micro nebulizer is increased and the "carry-over" of sample from one sample analysis procedure to a subsequent sample analysis procedure is easier to prevent because there is less internal volume to flush out between analysis procedures.

Users of the Fassel et al. micro nebulizer have found, however, that certain design features thereof make it inconvenient to use. For instance it is difficult to clean the device without completely breaking it down, and it is difficult to adjust the upper aspect of the inner tube, which inner tube carries a sample solution flow, with respect to the upper aspect of the outer tube thereof. It is noted that the annular space between the outer surface of the inner tube and the inner surface of the outer tube provides a pathway through which a gas flow is maintained during use of the micro nebulizer. Said gas flow interacts with the sample solution flow at the location at which both flows simultaneously eject from the upper aspect of the micro nebulizer to cause the sample solution to be nebulized into sample solution droplets. The two flows alluded to, it will be appreciated, must eject at proper orientations with respect to one another or proper sample solution nebulization is not achieved. The utility of an ability to easily adjust the vertical location of the upper aspect of the inner tube with respect to that of the outer tube should then be appreciated. It has also been found that the inner tube of the Fassel et al. invention can be easily crushed, for example when the invention is being cleaned. A separate or integral protective sleeve which covers at least a portion thereof would therefore provide utility. Additionally, it is taught herein that the major aspect of the direct injection micro nebulizer system should preferably be of one piece unibody construction, should contain no metallic parts and be of a material which is resistant to degradation by hydrofloric acid. The later aspects of the design are related to the occurance of untoward effects when the invention is placed near an inductively coupled plasma, and to the fact that samples to be nebulized at times are solvated by a solvent containing hydrofloric acid or the fact that hydrofloric acid is sometimes used as a cleaning agent in analysis systems.

In addition, the present invention provides that the direct injection nebulizer system should be designed to allow use with not only standard ICP torch sample analysis systems, but also with ICP torches which have no sample injector tube present or with other sample analysis systems such as mass spectrometer sample analysis systems. That is, the direct injection micro nebulizer system should not require attachment to the sample injector tube of a standard ICP torch to be utilized.

An improved micro nebulizer system, termed a Direct Injection Micro Nebulizer System, is thus taught herein, which serves to overcome the problems inherent in the use of the Fassel et al. invention.

It is therefore a purpose of the present invention to provide a direct injection micro nebulizer system which is easy to clean.

It is another purpose of the present invention to provide a direct injection micro nebulizer system in which adjustment of the vertical location of the upper aspect of the inner, sample delivery, tube with respect to the outer tube, (termed a primary body element in the present invention), is easy to carry out.

It is yet another purpose of the present invention to teach a direct injection micro nebulizer system which is constructed from nonmetalic and/or hydrofloric acid resistant materials.

It is still yet another purpose of the present invention to teach a direct injection micro nebulizer system which provides one piece or unibody construction of the major element, the primary body element, of the invention.

Still yet another purpose of the present invention is to teach the use of a separate or integral protective sleeve on the sample delivery,(i.e. inner tube of Fassel et al. invention), tube to form a crush resistant sample delivery tube system.

Yet still another purpose of the present invention is to teach a direct injection micro nebulizer system which can be used in sample analysis systems which do not provide a sample injector tube of a standard ICP torch as an element thereof.

BRIEF DESCRIPTION OF THE DRAWINGS

FIG. 1a shows a side elevational view of one embodiment of the present invention in cross section, as viewed from a position perpendicularly removed therefrom.

FIG. 1b shows a perspective view of a portion of a sample delivery tube system of the present invention.

FIG. 2 shows a side elevational view of a standard torch used in inductively coupled plasma analysis of samples, with the present invention present in the sample injector tube thereof, viewed from a position perpendicularly removed therefrom.

FIG. 3 shows a portion of the present invention oriented horizontally in cross section, with block diagrams representing sample analysis system elements other than an inductively coupled plasma standard torch.

DETAILED DESCRIPTION

Figure 4:
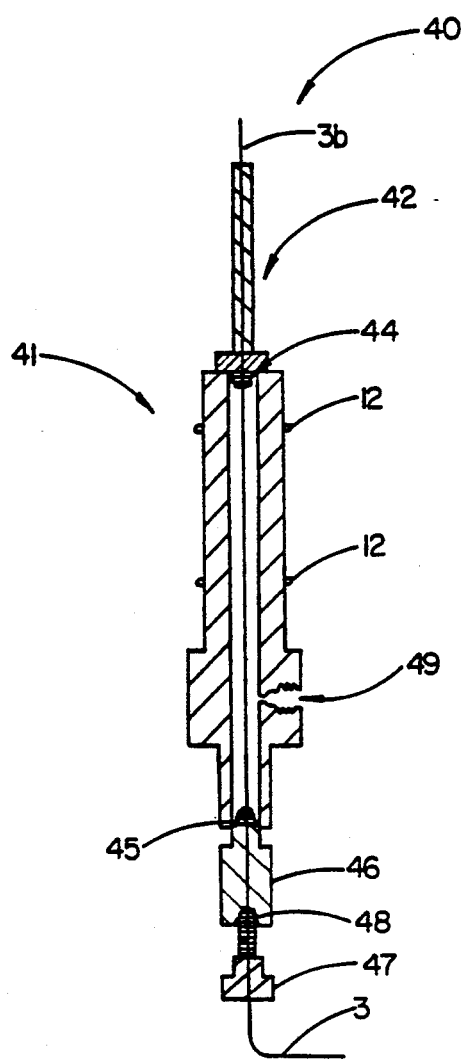
FIG. 4 shows a side elevational view of a modified embodiment of the present invention in cross section, as viewed from a position perpendicularly removed therefrom.

Turning now to the drawings, there is shown in FIG. 1a one embodiment of the present invention (10), in cross sectional elevation as viewed from a position perpendicularly removed therefrom with the longitudinal dimension thereof projecting vertically upward from an underlying horizontal surface. In particular note that there is shown a primary body element (1), typically of unibody construction, a top element (2), a double nut element system (11) comprised of upper nut (8) and lower nut (7), a sample delivery tube system (3) comprised of a sample delivery tube (3b) and a protective sleeve (3a), and an "O" ring (12). FIG. 1b shows an enlarged view of a portion of the sample delivery tube system (3) in perspective, showing that the sample delivery tube system (3) can be comprised of a sample delivery tube (3b) and a protective sleeve (3a) through which the sample delivery tube (3b) is threaded, over at least a portion of its length. Said protective sleeve (3a) serves to protect the sample delivery tube (3b) against being crushed. (It is mentioned that a high strength crush resistant sample delivery tube (3b) per se. could alone comprise a sample delivery tube system (3) with the protective sleeve (3a) being an integral component thereof). It is also possible to provide sample delivery tube system (3) with a temperature control element such as an ohmic high resistance electrical conducting coil wound therearound along at least a portion of its length, (similar to the shown protective sleeve (3a)), so that during use of the direct injection micro nebulizer (10) in a sample analysis procedure the temperature of said sample delivery tube system (3) can be controlled. Controlling the temperature thereof can lead to a decreased tendency of sample solids to adhere to and deposit inside the sample delivery tube (3b) during use. As a result a lessened chance that the sample delivery tube system (3) will become clogged is achieved. It is noted that the sample delivery tube (3b) is typically fifty (50) micrometers inner diameter and one-hundred-eighty (180) micrometers outer diameter. As well, the primary body element (1) is typically approximately one-hundred (100) milimeters in length. These dimensions are exemplary and not limiting, however.

Continuing, note that the top element (2), primary body element (1) and upper and lower nuts (6) and (7) respectively have centrally located longitudinally oriented holes therethrough, through which the sample delivery tube system (3), or at least the sample delivery tube (3b) per se can be threaded. (Note, the term "centrally located" is to be taken to mean that when the various elements of the present invention are properly attached to one another, the longitudinally oriented holes through them line up with one another so as to provide a continuous hole through the assembled direct injection micro nebulizer system). It is noted that the inner diameter of the centrally located longitudinally oriented hole through the top element (2) is typically, but not necessarily, two-hundred (200) micrometers. As a result the annular space between the outer surface of the sample delivery tube and the inner surface of the centrally located longitudinally oriented hole through the top element (2), when the sample delivery tube (3b) is threaded therethrough, is only approximately ten (10) micrometers radially. Also note that the primary body element (1) has, at its upper aspect, a first connection means (4), typically comprised of female screw threads, which first connection means interacts with complimentary connection means on the lower aspect of top element (2) to removably attach top element (2) to said primary body element (1). The primary body element (1) also provides a second connection means (5), at the lower aspect thereof, typically female screw threads, which second connection means (5) interact with complimentary connection means on the upper aspect of upper nut (6) of the double nut system (11), to removably attach upper nut (6) to the lower aspect of the primary body element (1). The lower aspect of the upper nut (6) provides connection means (8), typically female screw threads, which connection means interact with complimentary connection means at the upper aspect of the lower nut (7) to removably attach said second nut (7) to said first nut (6). The primary body element also presents a third connection means (9), typically female screw threads, which allows attachment thereof to a source of gas flow, which gas flow is identified as "G" in FIG. 2. Said third connection means (9) provides access to the centrally located space of the centrally located longitudinally oriented hole which is present through the primary body element (1), which space is designated (1s), by way of access port (9p).

It is to be understood that sample delivery tube system (3) is caused to be firmly, but removably, secured to the lower nut (7) of the double nut element system (11). This is typically accomplished by providing a tapering female screw thread connection means at the lower aspect of the upper nut (6), into which complimentary connection means, comprising male screw threads at the upper aspect of the lower nut (7), can screw. As the complimentary connection means are caused to be screwed into the connection means (8) at the lower aspect of the upper nut (6), the centrally located hole through lower nut (7) is caused to collapse to some extent and firmly grasp said sample delivery tube system (3). It is also to be understood that the second connection means (5) at the lower aspect of the primary body element (1) allows complimentary connection means at the upper aspect of upper nut (6) to be manipulated with respect to the second connection means (5) on primary body element (1), so that the vertical location of the upper aspect of sample delivery tube (3b) can be precisely adjusted, when the sample delivery tube (3b) is threaded through the entire direct injection micro nebulizer system as shown in FIG. 1a. Said manipulation typically comprises turning of upper nut (6) with respect to primary body element (1), although any functionally equivalent system can be used.

It should be also appreciated that the first connection means (4) at the top of primary body element (1) allows a user of the present invention to easily gain access to the upper aspect of the space (1*s*) withing the primary body element (1) by removal of top element (2). This allows easy threading of sample delivery tube (3*b*), and easy cleaning of any sample solids which might accumulate within the space (1*s*) of the primary body element (1) during use in a sample analysis procedure. Said sample solids accumulation would, for instance, occur if the upper aspect of the sample delivery tube (3*b*) were not threaded through the longitudinally oriented centrally located hole in the top element. This would configure the system very much like the system shown in the Fassel et al. Patent. It is noted, however, that the preferred arrangement of the present invention provides that the upper aspect of the sample delivery tube (3*b*) be threaded through the centrally located longitudinally oriented hole which transverses the top element (2).

The preferred materials from which the present invention is constructed are hydrofloric acid resistant and nonmetallic. This is important as some sample solids are solvated in solvent containing hydrofloric acid, and metals can interact with energy fields when the direct injection micro nebulizer is placed into an inductively coupled plasma analysis system, discussed below with respect to FIG. 2. Said interaction can cause untoward effects.

Turning now to FIG. 2, there is shown a side elevational view, as viewed from a position perpendicularly removed therefrom, of a standard torch (20) used with Inductively Coupled Plasma sample analysis systems, with the present invention (10) shown placed therein. Note the presence of an outer tube (21), intermediate tube (22) and sample injector tube (23), as well as an outer port (16), intermediate port (17), auxiliary sample flow port (19) and a sample injector port (23*p*). When the standard torch (20) is used without the present invention (10) present therein, a liquid sample flow "C" is entered at the sample injector port (23*p*), and caused, typically under the influence of a pressure gradient, to flow vertically through the sample injector tube (23) and eject into the space above the vertically upper aspect of the sample injector tube, which space is designated as (25), at which location a plasma is typically caused to exist during use. Note it is also possible to induce sample flow by application of an electric potential between the upper and lower extents of the sample delivery tube, said voltage constituting a functionally equivalent pressure gradient. Such an interpretation is to be considered within the scope of the claims. Vertically or tangentially directed gas flows "A" and "B" are entered at the outer and intermediate ports (16) and (17) respectively, and under the influence of pressure gradient move upward through the spaces of the standard torch (20) into which they are injected. Typically tangentially directed flows are used in which the gas follows a vertically upward spiral-like motion. The purposes of said injected gas flows "A" and "B" are to shield the components of the standard torch (20), (eg. (21), (22) and (23)), which they contact against the temperature and heat produced by a created plasma, and to aid the sample entry flow "C" into said plasma. It is mentioned that normally the auxiliary sample flow port (19) will not be used when the standard torch (20) is used without the present invention (10) present therein.

Now, FIG. 2 shows the present invention (10) as inserted into the space within the sample injector tube (23) of the standard torch (20). In use the typically tangentially injected gas flows "A" and "B" at outer and intermediate ports (16) and (17) respectively will again be injected for purposes similar to those described above. With the present invention (10) present, however, a sample solution is entered into the sample delivery tube (3b) and caused to flow through the length of said sample delivery tube (3b) and eject from the vertically upper aspect thereof into the space (25) of the standard torch (20) in which a plasma can be created. Note that the sample solution is not nebulized prior to entry to the sample delivery tube (3b). In addition, a gas flow "G" is injected into port (9p) of the primary body element (1) and caused to flow through the annular space (1s) within the centrally located longitudinally oriented hole which vertically transverses the primary body element, between the outer surface of the sample delivery tube system (3) and the inner surface of the centrally located longitudinally oriented hole through the primary body element (1), and out thereof between the annular space between the outer surface of the sample delivery tube (3b) and the inner surface of the longitudinally oriented centrally located hole which is present through the top element (2). Interaction of the sample solution flow "C" and the gas flow "G" where both eject from the vertically upper aspect of the present invention causes nebulization of the sample solution to occur. Said nebulization can be aided by injection of an auxiliary sample gas flow "F" at auxiliary sample port (19) of the standard torch (20), which gas flow "F" ejects from the annular space between the outer surface of the primary body element (1) of the present invention and the inner surface of the sample injector tube (23) of the standard torch (20) and helps further nebulize, and to sweep, the nebulized sample flow created by interaction of flows "C" and "G" upward into space (25) of the standard torch (20).

Also note the presence of an "O" ring (12) around the outer surface of primary body element (1). Said "O" ring (12) serves to firmly secure the present invention (10) inside the sample injector tube of the standard torch (20).

Turning now to FIG. 3, there is shown a partial view of the present invention (10), oriented with the longitudinal dimension thereof projecting horizontally so that top element (2) is at the right of the primary body element (1) in said figure. Also shown are blocks (31) and (32). Said blocks represent, generally, elements of sample analysis systems other than those that use Inductively Coupled Plasmas and standard torches, as were described above. Block (31) for instance, might represent a vacuum desolvation chamber, and block (32) a mass spectrometer.

It is not the purpose of the present disclosure to teach the operation of various sample analysis systems, but only to disclose a new total consumption direct injection micro nebulizer system which can be used with various sample analysis systems. The claims are to be interpreted so as to include use of the presently disclosed invention with any sample analysis system.

Finally, as regards FIGS. 1 and 2, the double nut element system (11) of the present invention demonstrates a means by which the vertical level of the upper aspect of the sample delivery tube system (3) can be easily and conveniently adjusted without the requirement that the present invention system be dismantled. Any functionally equivalent sample delivery tube system adjustment means is to be considered as within the scope of the claims.

Turning now to FIGS. 4 and 5, there is shown a modified embodiment of the present invention and torch. FIG. 4 shows a direct injection micro nebulizer system (40) which is functionally similar to that described with respect to FIG. 1*a*, but with design modifications present. Generally, primary body element (41) provides first, second and third connection means (44), (45) and (49) respectively. Top element (42) attaches to first connection means (44) as does top element (2) attach to first connection means (4) in FIG. 1, but top element (42) has present an elongated portion, (eg. approximately seventy (70) milimeters long), which is not present in top element (2). In addition it is noted that the primary body element (41) is typically, but not necessarily, approximately one-hundred (100) milimeters long and approximately fifteen (15) milimeters outer diameter at the point at which it enters a torch as shown in FIG. 5. Reference to FIG. 5 shows that the elongated portion of top element (42) allows positioning sample delivery tube (3*b*) which threads therethrough near the location (55) in torch (50) where a plasma can be formed during use, without positioning the vertically upper aspect of primary body element (41) near thereto. Also shown in FIG. 4 are upper nut (46) and lower nut (47), the system of which allows easy adjustment of the vertical level of the upper aspect of the sample delivery tube (3*b*). Upper nut (46) attaches to second connection means (45) of the primary body element (41), and lower nut (47) attaches to the upper nut (46) by means of connection means (48). Sample delivery tube system (3) is firmly gripped by lower nut (47), and adjustment of the connection between the primary body element (41) and the upper nut (46) allows easy adjustment of the vertical level of the upper aspect of the sample delivery tube (3*b*). Third connection means (49) allows attachment to a source of gas flow shown as "G" in FIG. 5. Interaction between sample flow "C" and gas flow "G" where both eject from the upper aspect of top element (42) causes sample nebulization. Note that FIG. 5 shows a torch (50) which does not have a sample injector tube analogous to sample injector tube (23) in FIG. 2. As a result there is no provision for a gas flow analogous to gas flow "F" shown in FIG. 2. The torch of FIG. 5 secures the primary body element (41) of the present invention within intermediate tube (52) by way of "O" rings (12), which "O" rings are typically present as a pair thereof. The outer tube (51) is analogous to outer tube (21) of FIG. 2 and ports (56) and (57) are analogous to ports (16) and (17) in FIG. 2. Gas flows "A" and "B" are similar in both FIGS. 5 and 2. It is noted that when the torch (50) is used, it is possible to remove the direct injection micro nebulizer (40) therefrom and insert a separate sample injector tube assembly. FIG. 6 shows a modular sample injector tube system (60) with substitute primary body element (41*p*) and sample injector tube (42*p*) present. This allows easy convertability of the torch from one which uses the present invention to one which allows use of sample nebulized by other (eg. pneumatic, ultrasonic etc.) means at a distal location.

Figure 5:
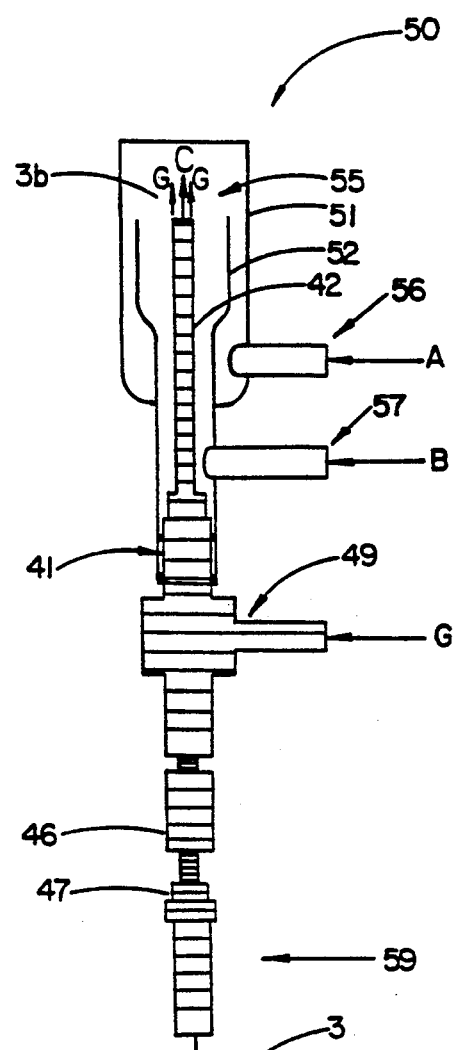
FIG. 5 shows a side elevational view of a specially designed torch used in inductively coupled plasma analysis of samples, with the modified embodiment of the present invention present within the intermediate tube thereof, viewed from a position perpendicularly removed therefrom.
Figure 6:
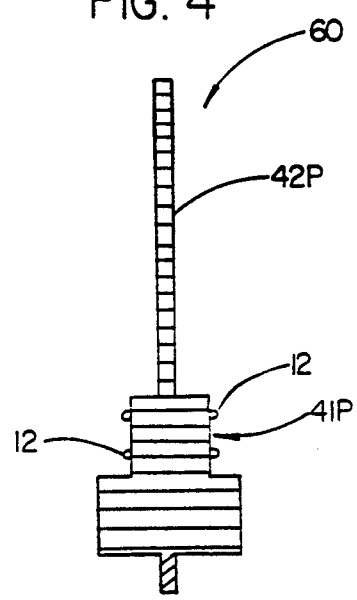
FIG. 6 shows a modular sample injector tube system which can be placed in the specially designed torch of FIG. 5 in place of the modified embodiment of the present invention of FIG. 4 when it is desired to utilize sample solution nebulizing means located distally from the sample analysis system.

Finally, FIG. 5 shows lower nut (47) as being coupled to a chromatography column (59). When this, or equivalent, configuration is present, a sample solution "C" entered to the sample delivery tube (3b) will typically contain multi-analyte components. The chromatography column (59) will cause temporal separation of the various analyte components in a solution passed therethrough, based upon differing transport characteristics of each analyte component in the chromatography column. As a result, a single sample analysis procedure might be able to identify a sequence of sample analyte components very easily and conveniently. Chromatography, it is mentioned, is a well known technique for providing a means for separating sample analyte components in a multi component sample solution as said sample solution is passed through a chromatography column.

Having hereby disclosed the subject matter of the present invention, it should be obvious that many modifications, substitutions, and variation of the present invention are possible in light of the teachings. It is therefore to be understood that the invention may be practiced other than as specifically described, and should be limited in breadth and scope only by the claims.

I claim:

1. A direct injection micro nebulizer system comprising:
   a primary body element,
   a sample delivery tube system, and
   a sample delivery tube system adjustment means;
   said primary body element being of a generally elongated shape presenting with a longitudinal dimension and having a first connection means at an upper aspect thereof, with upper aspect being defined as the vertically higher end of the primary body element as viewed in side elevation from a position perpendicularly removed therefrom while the longitudinal dimension thereof projects vertically upward and perpendicular to an underlying horizontal surface; and said primary body element also having a second connection means at a lower aspect thereof, and a third connection means thereon;
   said sample delivery tube system comprising, at a minimum, a sample delivery tube;
   said sample delivery tube system adjustment means being connected to said primary body element at the second connection means thereof;
   said primary body element and sample delivery tube system adjustment means having centrally located longitudinally oriented holes therethrough;
   said sample delivery tube system being threaded into the centrally located longitudinally oriented hole in the sample delivery tube system adjustment means and through the centrally located longitudinally oriented hole through the primary body element so that the upper aspect of the sample delivery tube is at a position near the upper aspect of the primary body element;
   the position of the upper aspect of said sample delivery tube being precisely adjustable by manipulation of the sample delivery tube system adjustment means;
   said sample delivery tube allowing a sample solution to be entered thereto at a lower aspect thereof and forced to flow through said sample delivery tube to the upper aspect thereof;
   said third connection means on the primary body element allowing gas to be entered into and be forced to flow through the annular space formed between the outer surface of the sample delivery tube and the inner surface of the centrally located longitudinally oriented hole through the primary body element;
   such that during use said sample solution flow and said gas flow are simultaneously ejected from the upper aspects of the sample delivery tube and the annular space between the outer surface of the sample delivery tube and the inner surface of the centrally located longitudinally oriented hole through the primary body element respectively, and interact with one another such that the sample solution is caused to be nebulized.

2. A direct injection micro nebulizer system as in claim 1, which further comprises a top element having a centrally located longitudinally oriented hole therethrough, said top element being attached to the first connection means of the primary body element by way of complimentary connection means thereon, with said sample delivery tube being threaded through the centrally located longitudinally oriented hole in said top element so that the upper aspect thereof is positioned beyond the upper aspect of the top element, such that the gas which flows through the annular space between the outer surface of the sample delivery tube and the inner surface of the centrally located longitudinally oriented hole through the primary body element ejects from the annular space between the outer surface of the sample delivery tube and the inner surface of the centrally located longitudinally oriented hole through the top element during use.

3. A direct injection micro nebulizer system as in claim 2, in which said primary body element and top element, are constructed from hydrofluoric acid resistant nonmetallic material.

4. A direct injection micro nebulizer system as in claim 1, which further comprises a chromatography column which is attached to the sample delivery tube system, through said chromatography column a sample solution flows prior to flowing through the sample delivery tube.

5. A direct injection micro nebulizer system as in claim 1, in which said sample delivery tube system includes, along at least a portion of its length, a temperature control element for use in controlling the temperature thereof and sample flowing therethrough during use.

6. A direct injection micro nebulizer system as in claim 1, which further comprises a protective sleeve along at least a portion of its length, to prevent crushing of said sample delivery tube.

7. A direct injection micro nebulizer system as in claim 1, in which the first, second and third connection means of the primary body element comprise female screw threads.

8. A direct injection micro nebulizer system as in claim 2, in which the top element and the sample delivery tube system adjustment means are attached to the primary body element at the first and second connection means thereof respectively in a manner which allow easy removal thereof.

9. A direct injection micro nebulizer system as in claim 1, in which the first connection means of the primary body element is simply the upper aspect of the longitudinally oriented centrally located hole through said primary body element.

10. A direct injection micro nebulizer system as in claim 1 in which the sample delivery tube system adjustment means comprises a double nut system, with the first nut thereof having connection means complimentary to the second connection means of the primary body element, and the second nut thereof having connection means thereon which are complimentary to additional connection means in the first nut thereof and means for firmly securing the sample delivery tube system such that when the two nuts are connected to one another, and the combination is connected to the primary body element at the second connection means thereof, adjustment of the first nut connection in the second connection means of the primary body element causes the position of the upper aspect of the sample delivery tube to be precisely adjusted with respect to the upper aspect of the primary body element.

11. A direct injection micro nebulizer system as in claim 1 which further comprises a standard torch of the type used in inductively coupled plasma analysis of samples, in combination with the direct injection micro nebulizer system, which standard torch comprises:

an outer tube which concentrically encompasses an intermediate tube, which intermediate tube concentrically encompasses a sample injector tube, each of which tubes is of a generally elongated shape and presents with a longitudinal dimension;

outer, intermediate, sample and auxiliary sample flow ports;

said outer port providing access to the annular space between the outer surface of the intermediate tube and the inner surface of the outer tube;

said intermediate port providing access to the annular space between the outer surface of the sample injector tube and the inner surface of the intermediate tube; and said sample and sample auxiliary sample flow ports providing access to the space within the sample injector tube, said sample flow port being located at the lower aspect of the standard torch, with lower aspect being defined as the vertically lower end of said standard torch as it is viewed in side elevation from a position perpendicularly removed therefrom, with the longitudinal dimensions of the various tubes projecting vertically upward, perpendicular to an underlying horizontal surface;

said direct injector micro nebulizer system being inserted into the space within the sample injector tube of the standard torch by way of the sample flow port at the lower aspect thereof thereby becoming concentrically encompassed by the sample injector tube;

said outer and intermediate flow ports allowing entrance of gas flows which serve to protect the tubes of the standard torch which they contact against the high temperatures and heat of a plasma which can be created inside the outer tube at the upper aspect of said standard torch, and to aid nebulized sample to flow thereto; and said auxiliary sample gas flow port allowing entry of a gas flow into the annular space between the outer surface of the direct injection micro nebulizer system and the inner surface of the sample injector tube, which gas flow interacts with the nebulized sample flow created by interaction of the ejected sample solution and the gas flow entered to sample delivery tube and the third connection means of the primary body element of the direct injection micro nebulizer system respectively, to further nebulize the sample and to aid its flow into the upper aspect of the standard torch wherein a plasma can be created for use in the analysis of the nebulized sample.

12. A direct injection micro nebulizer system as in claim 1 which further comprises a specially designed torch of the type used in inductively coupled plasma analysis of samples, in combination with the direct injection micro nebulizer system, which specially designed torch comprises:

an outer tube which concentrically encompasses an intermediate tube, each of which tubes is of a generally elongated shape presenting with a longitudinal dimension;

outer, intermediate and sample flow ports;

said outer port providing access to the annular space between the outer surface of the intermediate tube and the inner surface of the outer tube;

said intermediate and sample flow ports providing access to the space within the intermediate tube, said sample flow port being located at the lower aspect of the specially designed torch, with lower aspect being defined as the vertically lower end of said specially designed torch as it is viewed in side elevation from a position perpendicularly removed therefrom, with the longitudinal dimensions of the various tubes projecting vertically upward, perpendicular to an underlying horizontal surface;

said direct injection micro nebulizer system being inserted into the space within the intermediate tube of the specially designed torch by way of the sample flow port therein thereby becoming concentrically encompassed by the intermediate tube;

said outer port allowing entrance of a gas flow which serve to protect the tubes of the specially designed torch which it contacts against the high temperatures and heat of a plasma which can be created inside the outer tube at the upper aspect of said specially designed torch, and said gas flow entered to the intermediate port serving to interact with the nebulized sample flow created by interaction with the sample solution and gas flows entered to lower aspect of the sample delivery tube and the third connection means of the primary body element of the direct injection micro nebulizer system respectively, to further nebulize the sample and to aid its flow into the upper aspect of the specially designed torch wherein a plasma can be created for use in the analysis of the nebulized sample.

13. A method of nebulizing a sample solution comprising the steps of:

a. obtaining a direct injection micro nebulizer system comprising:

a primary body element, a sample delivery tube system, and a sample delivery tube system adjustment means;

said primary body element being of a generally elongated shape presenting with a longitudinal dimension and having a first connection means at an upper aspect thereof, with upper aspect being defined as the vertically higher end of the primary body element as viewed in side elevation from a position perpendicularly removed therefrom while the longitudinal dimension thereof projects vertically upward and perpendicular to an underlying horizontal surface; and said primary body element also having a second connection means at a lower aspect thereof, aspect thereof, and a third connection means thereon;

said sample delivery tube system comprising, at a minimum, a sample delivery tube;

said sample delivery tube system adjustment means being connected to the primary body element at the second connection means thereof;

said primary body element and sample delivery tube system adjustment means being centrally located longitudinally oriented holes therethrough;

said sample delivery tube system being threaded into the centrally located longitudinally oriented hole in the sample delivery tube system adjustment means and through the centrally located longitudinally oriented hole through the primary body element so that the upper aspect of the sample delivery tube is at a position near the upper aspect of the primary body element;

the position of the upper aspect of said sample delivery tube being precisely adjustable by manipulation of the sample delivery tube system adjustment means;

said sample delivery tube allowing a sample solution to be entered thereto at a lower aspect thereof and be forced to flow through said sample delivery tube to the upper aspect thereof;

said third connection means on the primary body element allowing gas to be entered into and force to flow through the annular space formed between the outer surface of the sample delivery tube and the inner surface of the centrally located longitudinally oriented hole through the primary body element;

such that during use said sample solution flow and said gas flow are simultaneously ejected from the upper aspects of the sample delivery tube and the annular space between the outer surface of the sample delivery tube and the inner surface of the centrally located longitudinally oriented hole through the primary body element respectively and interact with one another such that the sample solution is caused to be nebulized;

b. entering a sample solution to the sample delivery tube at the lower aspect thereof and causing said sample solution to flow to the upper aspect of said sample delivery tube and eject therefrom while simultaneously entering a gas flow into the third connection means on the primary body element and causing it to flow through the annular space between the outer surface of the sample delivery tube and the inner surface of the centrally located longitudinally oriented hole through the primary body element and eject from the upper aspect of said annular space, thereat interacting with the simultaneously ejected sample solution flow in a manner which causes the sample solution to become nebulized.

14. A method of nebulizing a sample solution as in claim 13, which further comprises, prior to use of the direct injection micro nebulizer system to nebulize a sample solution, the step of attaching a top element to the primary body element of the direct injection micro nebulizer system, said top element having a centrally located longitudinally oriented hole therethrough and said top element being attached to the first connection means of the primary body element by way of complimentary connection means thereon, and said sample delivery tube being threaded through the centrally located longitudinally oriented hole in said top element so that the upper aspect thereof is positioned beyond the upper aspect of the top element, and said gas which flows in the annular space between the outer surface of the sample delivery tube and the inner surface of the centrally located longitudinally oriented hole through the primary body element ejects from the annular space which exists between the outer surface of the sample delivery tube and the inner surface of the centrally located longitudinally oriented hole through the top element.

15. A method of nebulizing a sample solution as in claim 13, which further comprises, prior to use of the direct injection micro nebulizer system to nebulize a sample solution, the step of precisely adjusting the position of the upper aspect of the sample delivery tube with respect to that of the primary body element by manipulation of the sample delivery tube system adjustment means.

16. A method of nebulizing a sample solution as in claim 13, which further comprises, prior to use of said direct injection micro nebulizer system to nebulize a sample solution, the step of providing the sample delivery tube system, along at least a portion of its length, with a temperature control element for use in controlling the temperature of said sample delivery tube system during use, and during use controlling said temperature control element so that the temperature of said sample delivery tube and sample flowing therein is maintained as desired by a user of the system.

17. A method of nebulizing sample solution as in claim 13, which further comprises the step of causing the sample solution to flow through a chromatography column prior to entering and flowing through the sample delivery tube.

18. A sample analysis system for use with direct injection micro nebulizer systems comprising a specially designed torch of the type used in inductively coupled plasma analysis of samples, which specially designed torch comprises:

an outer tube which concentrically surrounds an intermediate tube, each of said tubes being of a generally elongated shape presenting with a longitudinal dimension;

outer, intermediate and sample flow ports;

said sample flow and intermediate ports providing access to the space within the intermediate tube, said sample flow port being located at the lower aspect of the specially designed torch, with lower aspect being defined as the vertically lower end of said specially designed torch as viewed in side elevation from a position perpendicularly removed therefrom, with the longitudinal dimensions of the various tubes projecting vertically upward, perpendicular to an underlying horizontal surface;

said direct injection micro nebulizer system, during use thereof, being inserted into the space within the intermediate tube of the specially designed torch by way of the sample flow port, such that said intermediate tube thereby concentrically encompasses said direct injection micro nebulizer;

said intermediate flow port providing access to the annular space between the outer surface of the direct injection nebulizer system and the inner surface of the intermediate tube;

said outer flow port providing access to the annular space between the outer surface of the intermediate tube and the inner surface of the outer tube;

such that during use said outer and intermediate ports allow entrance of gas flows into the annular spaces within the specially designed torch said ports access, said gas flows serving to protect the tubes of the specially designed torch which they contact against the high temperatures and heat of a plasma which can be created inside the outer tube at the vertically upper aspect of said specially designed torch, and to aid nebulized sample to flow thereto.

19. A sample analysis system as in claim 18, in which the direct injection micronebulizer system can be removed from the intermediate tube and replaced with a modular sample injector tube system for use with sample solutions which are nebulized distally from the sample analysis system.

20. A direct injection micro nebulizer system as in claim 1, in which the longitudinal dimension of the primary body element is oriented vertically during use.

21. A direct inject micro nebulizer as in claim 1, in which the longitudinal dimension of the primary body element is oriented other than vertically during use.

22. A direct injection micro nebulizer system of the type including a sample delivery tube system concentrically encompassed within a centrally located longitudinally oriented hole through a primary body element of a generally elongated shape; in which the improvement comprises a sample delivery tube system adjustment mean which can be manipulated to precisely adjust the longitudinal position of the sample delivery tube system with respect to the concentrically encompassing primary body element, without the requirement that said direct injection micro nebulizer system be disassembled or subjected to potentially damaging fores.

23. A direct injection micro nebulizer system as in claim 22, in which all elements thereof are made of hydrofluoric acid resistant materials.

24. A direct injection micro nebulizer system as in claim 22, in which all elements thereof are made of non-metallic materials.

25. A direct injection micro nebulizer system of the type including a sample delivery tube system concentrically encompassed within a centrally located longitudinally oriented hole through a primary body element of a generally elongated shape presenting with a longitudinal dimension; in which the improvement comprises a top element which removably attaches to the upper aspect of said primary body element, with upper aspect defined to be the vertically higher end of the primary body element as viewed in side elevation from a position perpendicularly removed therefrom while the longitudinal dimension thereof projects vertically upward and perpendicular to an underlying horizontal surface, said top element having a centrally located longitudinally oriented hole therethrough through which the sample delivery tube system projects during use, removal of which top element allows easy access to the upper aspect of the centrally located longitudinally oriented hole through said direct injection micro nebulizer primary body element and facilitates the threading of the sample delivery tube system through the centrally located longitudinally oriented hole through said top element, without the requirement that said direct injection micro nebulizer system be subjected to any potentially damaging forces.

26. A direct injection micro nebulizer system as in claim 25, in which all elements thereof are made of hydrofluoric acid resistant materials.

27. A direct injection micro nebulizer system as in claim 25, in which all elements thereof are made of non-metallic materials.

* * * * *